United States Patent [19]

Ando et al.

[11] Patent Number: 4,520,008

[45] Date of Patent: May 28, 1985

[54] HAIR SETTING LOTION

[75] Inventors: Hiroshi Ando, Funabashi; Takeo Okumura, Sakura, both of Japan

[73] Assignee: Kao Soap Co., Ltd., Tokyo, Japan

[21] Appl. No.: 363,884

[22] Filed: Mar. 31, 1982

[30] Foreign Application Priority Data

Apr. 7, 1981 [JP] Japan ................................. 56-51977

[51] Int. Cl.$^3$ ........................... A61K 7/11; A61K 9/12
[52] U.S. Cl. .............................. 424/47; 424/DIG. 1;
424/70; 424/71; 424/78; 514/773
[58] Field of Search ............... 424/71, 70, 47, DIG. 1, 424/78, 359

[56] References Cited

FOREIGN PATENT DOCUMENTS 2003487 8/1970 Fed. Rep. of Germany ........ 424/47

OTHER PUBLICATIONS

Ash, A Formulary of Cosmetic Preparations, 1977, pp. 134–139.

Primary Examiner—Dale R. Ore
Attorney, Agent, or Firm—Oblon, Fisher, Spivak, McClelland & Maier

[57] ABSTRACT

There is disclosed a hair setting lotion which comprises a predetermined amount of a polymeric compound for setting the hair and a propylene oxide and ethylene oxide adduct of a higher alcohol. The adduct is contained in an amount of 0.05–1.0 time the polymeric compound on the weight basis. In order to further improve the hair setting effect, squalane can be added in an amount of 0.05–2.0 times the polymeric compound on the weight basis.

8 Claims, No Drawings

HAIR SETTING LOTION

BACKGROUND OF THE INVENTION

1. Field of the Invention

This invention relates to hair cosmetics and more particularly, to hair setting lotions which exhibit excellent curl retentivity and good texture of the hair after setting.

2. Description of the Prior Art

Cold perm treatments have widely been made so as to have the hair waved or curled. After the cold permanent waving, the hair is applied with hair setting lotions such as set lotions or hair sprays for the purpose of insuring the setting and beautiful styling of the hair. These hair setting lotions are also used to cause the hair, which has not been subjected to the cold perm treatment, to be transiently waved or curled or to prevent the hair from dishevelling.

These hair setting lotions have been heretofore produced by dissolving polymeric compounds for hair setting (hereinafter referred to simply as "polymeric compound") in a suitable solvent such as water, lower alcohols or mixed solvents of water and lower alcohols. The resulting solution is used as it is to give a setting lotion, and when a suitable liquefied gas is mixed with the solution as an injection to give an aerosol, this is used as a hair spray.

However, the conventional hair setting lotions thus obtained have the drawbacks (1) that since the surface tension of polymeric compounds is higher than the critical surface tension of the hair, they deposit on the hair as small lumps in the form of islands and do not form a uniform film, (2) that the polymer compound deposits on the hair as islands, so that the curl retentivity especially under high humidity conditions is poor and the texture is also poor, and (3) that the polymer compound deposited in the form of islands is liable to flake when the hair is combed, making the luster of the hair poor. In order to overcome the drawbacks, attempts have been made to add and incorporate oils for cosmetics, silicone oils, surface active agents and the like but are not satisfactory in results.

SUMMARY OF THE INVENTION

It is an object of the invention to provide a hair setting lotion which can overcome the drawbacks of the prior-art hair setting lotions.

It is another object of the invention to provide a hair setting lotion which exhibits much improved texture of the hair after setting and prolonged curl retention.

It is a further object of the invention to provide a hair setting lotion in which the specific type of propylene oxide and ethylene oxide adducts of higher alcohols are incorporated.

According to one aspect of the invention, there is provided a hair setting lotion which comprises the following ingredients (a) and (b):

(a) 0.2–10.0 wt% of a polymer compound; and
(b) a propylene oxide and ethylene oxide adduct of a higher alcohol contained in an amount of 0.05–1.0 time the ingredient (a) on the weight basis and represented by the formula (I)

in which R represents an aliphatic hydrocarbon group having 8–20 carbon atoms, n is a value of 10–50, and m is a value of 3–20.

According to another aspect of the invention, there is provide a hair setting lotion which comprises the following ingredients (a), (b) and (c):

(a) 0.2–10.0 wt% of a polymer compound;
(b) a propylene oxide and ethylene oxide adduct of a higher alcohol contained in an amount of 0.05–1.0 time the ingredient (a) on the weight basis and represented by the formula (I)

in which R, m and n have the same meanings as defined hereinbefore; and (c) squalane contained in an amount of 0.05–2.0 times the ingredient (a) on the weight basis.

DETAILED DESCRIPTION AND PREFERRED EMBODIMENTS OF THE INVENTION

The ingredient (a) of the invention is any polymer compounds used for conventional hair setting lotions and includes, for example, the following various compounds.

(1) Polyvinylpyrrolidone polymer compounds

There are mentioned as this class of the polymer compound polyvinylpyrrolidone, copolymers of vinyl pyrrolidone and vinyl acetate, terpolymers of vinylpyrrolidone, vinyl acetate and alkylaminoacrylates and the like which are commercially available in the name of Luviskol K, Luviskol VA, Luviflex D410I (Yuka-Badische Co., Ltd.) PVPK, PVP/VA, E-735 (GAF Co., Ltd.) and the like.

(2) Acidic vinyl ether polymer compounds

Lower alkyl half esters of copolymers of methylvinyl ether and maleic anhydride, commercially available under the name of Gantrez ES-225, ES-335 (GAF Co., Ltd.) can be mentioned.

(3) Acidic polyvinyl acetate polymer compounds

Copolymers of vinyl acetate and crotonic acid are mentioned and commercially available under the name of Resin 28-1310 (National Starch Co., Ltd.), Lviset CE5055 (Yuka-Badische Co., Ltd.) and the like.

(4) Acidic acryl polymer compounds

There are mentioned, for example, copolymers of acrylic acid and/or methacrylic acid and acrylic acid alkyl esters and/or methacrylic acid alkyl esters, and copolymers of acrylic acid, acrylic acid alkyl esters and N-alkylacrylamides. Commercially available products include Plascize (Gooh Chem. Co., Ltd.), Ultrahold 8 (Ciba-Geigy A.G.) and the like.

(5) Amphoteric acrylic polymer compounds

There are mentioned, for example, compounds obtained by copolymerizing dialkylaminoethyl methacrylates, dialkylaminoethyl acrylates and diacetoneacrylamide and acrylic acid, methacrylic acid, acrylic acid alkyl esters and methacrylic acid alkyl esters, and amphoterizing them with acetic halides and commercially available products include Ukaformer (AMPHOSET) AM-75 (Mitsubishi Petrochemical Co., Ltd.) and the like.

(6) Decomposition Derivatives of Keratin

The derivatives are those obtained by decomposing keratin materials by oxidation or decomposing keratin materials by reduction and chemically modifying thiol groups of the decomposition product.

The keratin materials include, for example, animal hair, human hair, feather, nail, horn, hoof, scale and the like, among which wool, human hair and feather are preferable.

The derivatives at the thiol groups are shown below:

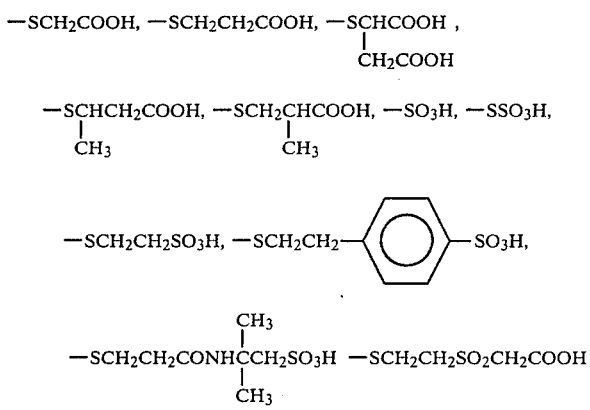

Among them, —SCH$_2$COOH and

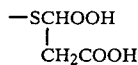

are preferable.

The chemical modification of the thiol groups can be made by any procedures known per se, for example, on the basis of procedures described in N. H. Leon: Textile Progress, Vol. 7, page 1 (1975), "Yuuki Ioo Kagoubutsu (Organic Sulfur Compounds)" written by Shigeru Daikyo (published by Kagaku Dojin (1968), and "Koubunshi Jikkengaku Koza" written by Masami Oku, Vol. 12, Kyoritsu Shuppan (1957).)

Among the polymer compounds of the ingredient (a), those having acidic groups should preferably be treated so that part or all (50 to 100%) of the acidic groups are neutralized from a viewpoint of the improvement of washability and texture. The alkalis employed for the neutralization are not critical and the acidic groups of the polymeric compound can be converted into salts of alkali metals such as sodium, potassium and the like, an ammonium salt, or salts of organic bases such as ethanolamine, diethanolamine, triethanolamine, 2-amino-2-methylpropanol, 2-amino-2-methyl-1, 3-propanediol, triisopropanolamine, glycine, histidine, alginine and the like. Of these, salts of 2-amino-2-methylpropanol and 2-amino-2-methyl-1, 3-propanediol are preferable.

Preferable polymer compounds are acidic acrylic polymer compounds (4) such as copolymers of diacetoneacrylamide, acrylic acid or methacrylic acid esters of fatty alcohols having 4-18 carbon atoms, or acrylic acid, methacrylic acid or itaconic acid and acrylic acid esters or methacrylic acid esters having 1-3 carbon atoms (Japanese Patent Publication No. 50-6538), and acrylic polymeric compounds of (5) including those obtained by copolymerizing monomers selected from the following three groups (i)-(iii) and subjecting the copolymer to the acetic halogenation treatment (Japanese Laid-open Publication No. 55-104209):

(i) dimethylaminoethyl methacrylate, diethylaminoethyl methacrylate, dimethylaminoethyl acrylate, N,N-dimethylethyl methacrylamide, 4-vinylpyridine and the like;

(ii) stearyl acrylate or methacrylate, lauryl acrylate or methacrylate, butyl acrylate or methacrylate, cyclohexyl acrylate or methacrylate, allyl methacrylate, ethyl acrylate or methacrylate, 2-ethylhexyl acrylate, and the like; and (iii) acrylonitrile, diacetone, acrylamide, styrene, chlorostyrene, vinyltoluene, vinyl acetate, hydroxyalkyl acrylate or methacrylate, an ester of polyethylene glycol or polypropylene glycol and acrylic or methacrylic acid, N-vinylpyrrolidone and the like.

In the practice of the invention, the ingredient (a) is made of one or more of the polymeric compounds and is contained in the hair setting lotion in an amount of 0.2–10.0 wt%, preferably 0.5–3 wt%.

The ingredient (b) is made of one or more propylene oxide and ethylene oxide adducts of higher alcohols and is contained in an amount of 0.05–1.0 time in weight the ingredient (a). Preferably ingredients (b) are those of the general formula (I) in which R is an alkyl group having 12 to 18 carbon atoms, n is a value of 20–40, and m is a value of 3–10.

The ingredient (c) used in a preferred embodiment of the invention is squalane having the following formula (II),

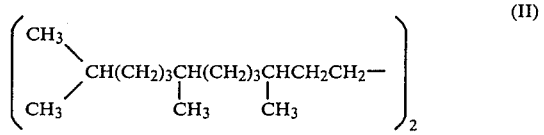

and is used in an amount of 0.05–2.0 times in weight the ingredient (a). Amounts smaller than 0.05 times are unfavorable since the set retentivity is not much improved as compared with the squalane-free composition, whereas amounts greater than 2.0 times are also unfavorable in view of the texture of the resulting composition since oiliness is emphasized.

The hair setting lotion according to the invention can be prepared by dissolving the above-described ingredients in a solvent such as water, a lower alcohol or a mixed solvent of water and a lower alcohol by a usual manner and, if necessary, mixing the solution with an propellant for aerosol.

The solvent is preferably water or a mixed solvent of a monohydric alcohol having 2–3 carbon atoms and water for the setting lotion and a monohydric alcohol having 2–3 carbon atoms and particularly ethanol for the hair spray.

The spray injection used for the hair spray includes, for example, chloroalkane or chlorofluoroalkane propellant such as trichloromonofluoromethane, dichlorodifluoromethane and the line, liquefied petroleum gas or mixtures thereof and is preferably charged in a pressure container in such a way that the inner pressure of an aerosol can after the charging is in the range of 2.0–4.0 kg/m$^2$G.

The propellant should be present in the hair setting lotion in an amount over 40% and preferably 50–80% or more.

To the hair setting lotion according to the invention may be added, aside from the above ingredients, within ranges not impeding the effect of the invention the following cosmetic oils; glycerides such as castor oil, cacao oil, mink oil, avocado oil, olive oil and the like, waxes such as beeswax, whale oil, lanolin, carnauba wax and the like; alcohols such as cetyl alcohol, oleyl alcohol, hexadecyl alcohol, lauryl alcohol, stearyl alcohol, isostearyl alcohol, 2-octyldodecanol, propylene glycol, polypropylene glycol, glycerine and the like; esters such as isopropyl myristate, hexyl laurate, cetyl lactate, propylene glycol monostearate, oleyl oleate, hexadecyl 2-ethylhexanoate, octyldodecyl myristate and the like; and silicone dervatives such as dimethylpolysiloxane, methylphenylpolysiloxane, polyethyer-modified silicone oils, epoxy-modified silicone oils, amino-modified silicone oils, alkyl-modified silicone oils and the like. In order to enhance the commercial value, perfumes or colorants may be added. Preservatives or antioxidants may be also added so as to prevent the composition from deteriorating as time goes.

The thus obtained hair setting lotion of the invention exhibits excellent curl retentivity and good texture of the hair after setting and these are emphasized especially when it is applied as a setting lotion or hair spray.

The present invention is particularly described by way of the following examples.

(1) Set Retentivity

A hair tress of 18 cm in length and 1.5 g in weight was wetted with water, wound about a rod, and air-dried. After the drying, the curled tress was removed from the rod, applied with each of the hair spray compositions for 5 seconds, and naturally dried. The curled hair was suspended in an air-conditioned chamber (25° C., 65%R.H.) for 1 hour and the degree of dilatation of the curled hair was observed to determine the set retentivity. The retentivity was determined such that the length of the hair which had been sprayed was taken as 100% set retentivity and the length of the curl-free, original hair (18 cm) was taken as 0% set retentivity.

(2) Texture, Stickiness

The hair tresses curled in the same manner as in (1) were applied with the individual hair spray compositions and naturally dried, which tresses were subjected to the sensory evaluation by 10 female panel members. The evaluation was shown by an average of evaluation points of the respective panel members.

| (Evaluation Point) | Content |
|---|---|
| +3 | Much better than control |
| +2 | Better than control |
| +1 | Slightly better than control |
| 0 | Equal to control |
| −1 | Slightly worse than control |
| −2 | Worse than control |
| −3 | Much worse than control |

TABLE 1

| | Propylene oxide and ethylene oxide adduct of higher alcohol (or comparative compound) | set Retentivity | Texture | Stickiness |
|---|---|---|---|---|
| Composition of Invention | In formula (1), $R = C_{12}$, $n = 45$, $m = 10$, | 67 | +2.3 | +2.2 |
| Comparative Composition | Diethyl phthalate | 40 | +0.6 | −0.8 |
| | Polyoxyethylene (20) sorbit monolaurate | 41 | +0.6 | +0.3 |
| | Propylene oxide and ethylene oxide adduct of lower alcohol (in formula (I) $R = C_4$, $n = 20$ and $m = 30$) | 50 | +0.6 | +0.3 |
| | Polyoxyethylene (10) cetyl ether | 50 | +1.3 | +1.1 |
| | Polyoxypropylene (15) cetyl ether | 45 | +0.4 | −0.2 |
| Control 1 | Nil | 31 | 0 | 0 |
| Control 2* | | 20 | +1.8 | +2.0 |

Control 2*: The same composition as the inventive composition except that polyvinylpyrrolidone is not contained.

EXAMPLE 1

Hair spray compositions of the following formulations were prepared and their set retentivity and texture of the hair applied were evaluated. The results are shown in Table 1.

| Formulation: | (wt %) |
|---|---|
| Polyvinylpyrrolidone (M.W. 40,000) | 2.0 |
| Propylene oxide and ethylene oxide adduct of higher alcohol (or comparative compounds) | 0.3 |
| Perfume | 0.1 |
| Absolute ethanol | balance |
| Trichlorofluoromethane | 30 |
| Dichlorodifluoromethane | 30 |

EXAMPLE 2

Hair spray compositions of the following formulations were prepared and evaluated in the same manner as in Example 1 with respect to the set retentivity, texture and stickiness. The results are shown in Table 2.

| Formulation: | (wt %) |
|---|---|
| Polymer compound | 2.0 |
| Propylene oxide and ethylene oxide adduct of higher alcohol | 0.2 (or 0) |
| Perfume | 0.2 |
| Absolute ethanol | balance |
| Trichlorofluoromethane | 30 |
| Dichlorodifluoromethane | 30 |

Tests:

Result:

TABLE 2

| | Polymer Compound | Propylene Oxide and Ethylene Oxide Adduct of Higher Alcohol | Set Retentivity | Texture | Stickiness |
| --- | --- | --- | --- | --- | --- |
| Composition of Invention | Gantrez ES225 (note 1) (GAF Co., Ltd.) | In formula (1), R = $C_{16}$, n = 30, m = 5 | 69 | +2.8 | +2.3 |
| | Vem 640 (note 2) (BARR-STALFORT CO., LTD) | In formula (1), R = $C_{16}$, n = 30, m = 5 | 68 | +2.2 | +2.9 |
| | Ukaformer AM75 (note 3) | In formula (1), R = $C_{16}$, n = 30, m = 5 | 74 | +2.5 | +2.9 |
| Control 1 | Gantrez ES225 | Nil | 32 | 0 | 0 |
| Control 2 | Vem 640 | Nil | 41 | 0 | 0 |
| Control 3 | Ukaformer AM75 | Nil | 42 | 0 | 0 |

(Note 1) Methyl vinyl ether/maleic anhydride copolymer
(Note 2) 90% neutralized product of vinylpyrrolidone/methacrylic acid/methacrylic ester copolymer with 2-aminomethylpropanol
(Note 3) Amphoterized product of dialkylaminoethyl methacrylate polymer with monochloroacetic acid

EXAMPLE 3

Hair spray compositions of the following formulations were prepared and evaluated in the same manner as in Example 1 with respect to the set retentivity, texture and stickiness. The results are shown in Table 3.

| Formulation: | (wt %) |
| --- | --- |
| Acrylic ester/methacrylic ester copolymer* | 1.0 |
| Propylene oxide and ethylene oxide adduct of higher alcohol (in formula (I), R = $C_{16}$, n = 20, m = 5) | 0.2 |
| Squalane | (Table 3) |
| Absolute ethanol | balance |
| Trichlorofluoromethane | 30 |
| Dichlorodifluoromethane | 30 |

*Placize L 53P, by Goo Chem. Co., Ltd.

Results:

TABLE 3

| Amount of Squalane (Wt %) | Set Retentivity** (%) | Texture | Stickiness |
| --- | --- | --- | --- |
| 0.02 | 60 | +2.2 | +2.2 |
| 0.05 | 72 | +2.3 | +2.9 |
| 0.5 | 77 | +3.0 | +2.6 |
| 1.0 | 71 | +2.8 | +2.0 |
| 0 | — | 0 | 0 |

**The set retentivity was determined after allowing to stand in an air-conditioned chamber of 25° C. and 98% R.H. for 1 hour.

What is claimed is:

1. A hair setting lotion comprising the following ingredients (a) and (b):
   (a) 0.2–10.0 wt% of a hair setting polymer compound selected from the group consisting of polyvinylpyrrolidone, copolymers of vinyl pyrrolidone and vinyl acetate, terpolymers of vinyl pyrrolidone, vinyl acetate and alkylaminoacrylates, lower alkyl esters of copolymers of methylvinyl ether and maleic anhydride, copolymers of vinyl acetate and crotonic acid copolymers of acrylic acid, arylic acid alkyl esters, acrylic acid alkyl esters, methacrylic alkylesters and acrylic acid, methacrylic acid, acrylic acid alkyl esters and acrylic acids methacrylic acid alkyl esters, methacrylic acid and acrylic acid alkyl esters, methacrylic acid and methacrylic acid alkyl esters and methacrylic acid, acrylic acid alkyl esters and methacrylic acid alkyl esters, copolymers of acrylic acid, acrylic acid alkyl esters and N-alkylacrylamides, amphoteric acrylic polymer compounds obtained by copolymerizing dialkylaminoethyl methacrylates, dialkylaminoethyl acrylates and diacetoneacrylamide and acrylic acid, methacrylic acid, acrylic acid alkyl esters and methacrylic acid alkyl esters and reacting the copolymers with acetic halides, and decomposition derivatives of keratin materials wherein the thiol groups of the decomposition derivative are at least one of

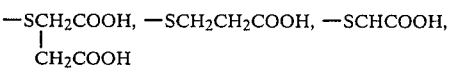

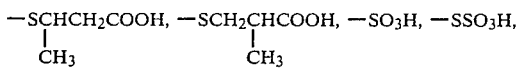

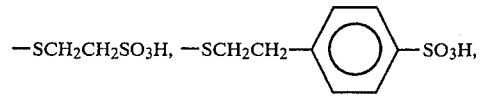

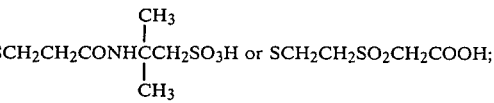

and
   (b) a propylene oxide and ethylene oxide adduct of a higher alcohol contained in an amount of 0.05–1.0 time the ingredient (a) on the weight basis and represented by the formula (I)

$$RO-(C_3H_6O)n(C_2H_4O)-_mH \qquad (I)$$

in which R represents an aliphatic hydrocarbon group having 8–20 carbon atoms, n is a value of 10–50, and m is a value of 3–20,
   the balance comprising a solvent selected from the group consisting of water, a lower alcohol and mixtures thereof.

2. A hair setting lotion according to claim 1, wherein said ingredient (a) is an acidic compound whose acidic groups comprise acidic groups which are partially or totally neutralized.

3. A hair setting lotion according to claim 1, wherein said ingredient (a) is selected from the group consisting of copolymers of acrylic acid and methacrylic acid and acrylic acid alkyl esters, copolymers of methacrylic acid and acrylic acid alkyl esters, copolymers of acrylic acid and acrylic acid alkyl esters, and copolymers of acrylic acid, acrylic acid alkyl esters and N-alkyl acrylamides.

4. A hair setting lotion according to claim 1, wherein said ingredient (a) is an amphoteric acrylic polymer selected from the group consisting of compounds obtained by copolymerizing dialkylaminoethyl methacrylates, dialkylaminoethyl acrylates and diacetoneacrylamide and acrylic acid, methacrylic acid, acrylic acid alkyl esters and methacrylic acid alkyl esters, and reacting said copolymers with acetic halides.

5. A hair setting lotion according to claim 1, wherein said ingredient (a) is contained in an amount of 0.5–3 wt% of the lotion.

6. A hair setting lotion according to any of claims 1, 2–5, further comprising squalane present in an amount of 0.05–2.0 times the ingredient (a) on the weight basis.

7. A hair spray comprising the hair setting lotion of claim 1 and a propellant, wherein said propellant is present in an amount of over 40%.

8. The hair setting lotion of claim 1, further comprising additives selected from the group consisting of cosmetic oils, perfumes, colorants, preservatives, antioxidants and mixtures thereof.

* * * * *